(12) United States Patent
Latterell et al.

(10) Patent No.: US 6,808,525 B2
(45) Date of Patent: Oct. 26, 2004

(54) BIPOLAR ELECTROSURGICAL HOOK PROBE FOR CUTTING AND COAGULATING TISSUE

(75) Inventors: Scott T. Latterell, Minneapolis, MN (US); Douglas S. Wahnschaffe, Otsego, MN (US)

(73) Assignee: Gyrus Medical, Inc., Maple Grove, MN (US)

( * ) Notice: Subject to any disclaimer, the term of this patent is extended or adjusted under 35 U.S.C. 154(b) by 161 days.

(21) Appl. No.: 10/225,321

(22) Filed: Aug. 21, 2002

(65) Prior Publication Data

US 2003/0040744 A1 Feb. 27, 2003

Related U.S. Application Data

(60) Provisional application No. 60/314,650, filed on Aug. 27, 2001, and provisional application No. 60/382,439, filed on May 22, 2002.

(51) Int. Cl.[7] .............................................. A61B 18/14
(52) U.S. Cl. ............................ 606/42; 606/47; 606/48; 606/50
(58) Field of Search ............................ 606/42, 46, 47, 606/48, 50

(56) References Cited

U.S. PATENT DOCUMENTS

| | | | |
|---|---|---|---|
| 2,002,594 A | 5/1935 | Wappler et al. | |
| 2,004,559 A | 6/1935 | Wappler et al. | |
| 4,209,017 A | 6/1980 | Shaw | |
| 4,311,143 A * | 1/1982 | Komiya | 606/47 |
| 4,492,231 A | 1/1985 | Auth | |
| 4,655,216 A | 4/1987 | Tischer | |
| 5,007,908 A * | 4/1991 | Rydell | 606/47 |
| 5,190,541 A | 3/1993 | Abele et al. | |
| 5,269,780 A | 12/1993 | Roos | |
| 5,282,799 A | 2/1994 | Rydell | |
| 5,330,470 A * | 7/1994 | Hagen | 606/42 |
| 5,443,463 A | 8/1995 | Stern et al. | |
| 5,445,638 A | 8/1995 | Rydell et al. | |
| 5,458,598 A | 10/1995 | Feinberg et al. | |
| 5,460,629 A * | 10/1995 | Shlain et al. | 606/46 |
| 5,484,435 A | 1/1996 | Fleenor et al. | |
| 5,573,535 A | 11/1996 | Viklund | |
| 5,599,350 A | 2/1997 | Schulze et al. | |
| 5,833,689 A * | 11/1998 | Long | 606/48 |
| 5,891,141 A | 4/1999 | Rydell | |
| 6,030,383 A | 2/2000 | Benderev | |
| 6,066,137 A | 5/2000 | Greep | |
| 6,206,876 B1 | 3/2001 | Levine et al. | |

* cited by examiner

*Primary Examiner*—Lee S. Cohen
(74) *Attorney, Agent, or Firm*—Thomas J. Nikolai; Nikolai & Mersereau, P.A.

(57) ABSTRACT

A bipolar electrosurgical hook probe includes an end effector that includes first and second electrodes placed in parallel, closely-spaced relationship, each being of a relatively large surface area and a conductive reciprocally movable hook member that is movable into and out of a space between the first and second electrodes. A switch mechanism is provided by which an RF current can alternatively be made to flow between the first and second electrodes during electrocoagulation and from the hook electrode to each of the first and second electrodes when the instrument is operating in its cut mode.

13 Claims, 2 Drawing Sheets

BIPOLAR ELECTROSURGICAL HOOK PROBE FOR CUTTING AND COAGULATING TISSUE

CROSS-REFERENCE TO RELATED APPLICATION

This application claims the benefit of U.S. Provisional patent Application Nos. 60/314,650, filed Aug. 27, 2001 and 60/382,439, filed May 22, 2002.

BACKGROUND OF THE INVENTION

I. Field of the Invention

This invention relates generally to electrosurgical instruments, and more particularly to an improved, bipolar, hook-probe for use in endoscopic surgery to provide enhanced cutting and coagulation capability over existing hook-probe instruments.

II. Discussion of the Prior Art

In the course of minimally invasive procedures, electrosurgery is often employed to effect cutting and coagulation or cauterization of tissue structures. The electrosurgical instruments employed have one or more electrodes adapted to be energized by RF currents. In so-called monopolar systems, the current passes from the instrument, through the tissue to be cut or coagulated to a body plate type return electrode located remote from the surgical site. Since the electrical currents tend to follow a path of least resistance from the instrument to the return electrode, the path is somewhat unpredictable and it has led to burns at unintended locations.

In the case of bipolar instruments, the active electrode and the associated return electrode are disposed in close proximity to one another on the instrument itself so that there is less likelihood of current flow to tissues other than intended tissue structures being operated upon. Bipolar electrosurgery is considered by most as a safer procedure.

In the Fleenor et al. U.S. Pat. No. 5,484,435, there is described a bipolar electrosurgical instrument intended for use in minimally invasive surgical procedures for both cutting and coagulating tissue, thus obviating the need for an instrument exchange where separate instruments as required for the cutting and coagulating functions. The instrument described in the '435 patent comprises a handle 98 disposed at one end of an elongated tubular barrel 96 having as one electrode a hook 90 in the form of a bent uninsulated wire and a one-piece return electrode 92 that is somewhat hemispherical in shape that projects outwardly from the distal end of the barrel and which has a slot formed therein for receiving the hook electrode therethrough. The walls of the slot are insulated so as to prevent short-circuiting with the hook member electrode but the portions of the electrode 92 on both sides of the slot are not insulated from each other. A lever assembly 98 on the handle, which when manipulated, allows the active hook electrode 90 to be extended and retracted relative to the fixed return electrode 92. In use, the active hook electrode is made to frictionally engage or slightly puncture target tissue to grip it. Then, by manipulating the lever 98 on the handle, the tissue can be drawn proximally to engage the return electrode. The electrosurgical generator is then activated to achieve cutting or coagulation.

The device of the '435 patent achieves acceptable levels of cutting because of the high current density present due to the small size and shape of the active electrode. However, coagulation with that instrument leaves much to be desired, given the small electrode surface area of the active electrode compared to that of the one-piece return electrode 92.

Bipolar coagulation devices require equal electrode surface area or a ratio of 1:1 for optimum results. Bipolar cut devices require a 4:1 or greater return electrode to active electrode ratio for effective precision cutting. Prior art bipolar devices have tended to be either good coagulators or good cutters, but not both.

The present invention is deemed to be a substantial improvement over the prior art as represented by the Fleenor et al. '435 patent. The device constructed in accordance with the present invention provides a hook probe that not only effectively cuts target tissue, but it also provides superior coagulation.

The Rydell U.S. Pat. No. 5,282,799 in the embodiment illustrated in FIG. 9 discloses an arrangement in which a pair of loop electrodes 28 and 30 are mounted on the distal end of a reciprocally movable control rod 60 that can be shifted longitudinally, via a thumb slide 224 so as to be extended from the distal tip of the instrument or retracted fully within the distal tip of the instrument. Also present on the insulating distal tip member 70 of the instrument are electrode surfaces 71 and 73. A push-button 216 moves longitudinally with the control rod so as to overlay a first dome switch 210 or a second dome switch 212. When the loop electrodes 28 and 30 are in their distalmost position projecting from the distal end of the instrument, the push-button 216 overlays the dome switch 210. Thus, when the push-button 216 is depressed, a cutting potential is applied between the electrodes 28 and 30. When the loop electrodes 28 and 30 are retracted by shifting the thumb slot in the proximal direction, the push-button 216 overlays the dome switch 212 so when it is depressed, a coagulating voltage is applied to the electrodes. Since the loop electrodes are retracted into a recess in the distal tip, they are not exposed to tissue. Only tissue bridging the surface contacts 71 and 73 will have a coagulating current flowing through it.

In this design, when electrosurgical cutting is involved, the same cutting voltage that is applied to the loop electrodes 28 and 30 is also present between the surface-mounted coagulating electrodes 71 and 73. The surgeon must, therefore, exercise increased caution to avoid inadvertent contact of non-target tissue with the surface electrodes as the cutting operation is taken place.

The Rydell U.S. Pat. No. 5,891,141 describes an electrosurgical instrument for cutting and coagulating tubular tissue structures, such as vein and arterial tissue, by grasping the tissue between a pair of spaced-apart electrodes that when energized by RF energy coagulates the portion of the tissue structure contained between the two electrodes. Once desiccated, a thumb switch is manipulated to cause a cutting blade to mechanically cut through the desiccated tissue.

The Roos U.S. Pat. No. 5,269,780 describes an electrosurgical instrument designed to both cut and coagulate tissue. It includes a handle having a pair of stationary L-shaped hook electrodes 22 and 23 projecting from a distal end of the handle in parallel, spaced-apart relation. These electrodes function to coagulate tissue and once coagulated, a cutting electrode 21 is made to descend into the gap between the two stationary electrodes while a cutting voltage is applied between it and the two stationary coagulating electrodes which function as a neutral. No provision is made for retracting any of electrodes 21–23 into the handle member.

SUMMARY OF THE INVENTION

The foregoing objects and advantages of the present invention are provided by designing a bipolar electrosurgical cutting and coagulating probe that has an elongated, tubular barrel with a proximal end, a distal end and a lumen extending between the two. A handle member is affixed to the proximal end of the barrel and an end effector is affixed to its distal end. The end effector in accordance with the present invention includes first and second electrodes that are placed in parallel, closely-spaced, non-contacting relationship where each is of a relatively large surface area. A conductive, reciprocally movable hook member is operatively coupled to a mechanism on the handle member so that manipulation of the mechanism causes the hook member to be movable in and out of the space separating the first and second electrodes from one another. The hook member has a relatively small surface area compared to the combined surface area of the first and second electrodes. A plurality of elongated conductors extends through the handle and into the lumen of the barrel, the first being electrically connected to the first electrode, the second to the second electrode and the third to the hook member electrode. In its cut mode, an appropriate RF voltage is applied between the hook electrode and the first and second electrodes as tissue comes into contact with all three electrodes or is gripped by the hook drawn toward and against the first and second electrodes which together function as the return electrode for the bipolar instrument. When operating in a coagulation mode, however, the RF voltage is only applied between the first and second electrodes. The hook is not energized. Because the first and second electrodes are of generally equal surface area, coagulation occurs over the entire active surfaces of the first and second electrodes, providing appreciably greater margins than result from the Fleenor-type instrument, There are, of course, additional features of the invention that will be described hereinafter which will form the subject matter of the appended claims. Those skilled in the art will appreciate that the preferred embodiments may readily be used as a basis for designing other structures, methods and systems for carrying out the several purposes of the present invention. It is important, therefore, that the claims be regarded as including such equivalent constructions since they do not depart from the spirit and scope of the present invention. The foregoing and other features and other advantages of the invention will be apparent from the following more particular description of preferred embodiments of the invention, as illustrated in the accompanying drawings.

DESCRIPTION OF THE PREFERRED EMBODIMENT

Figure 1:
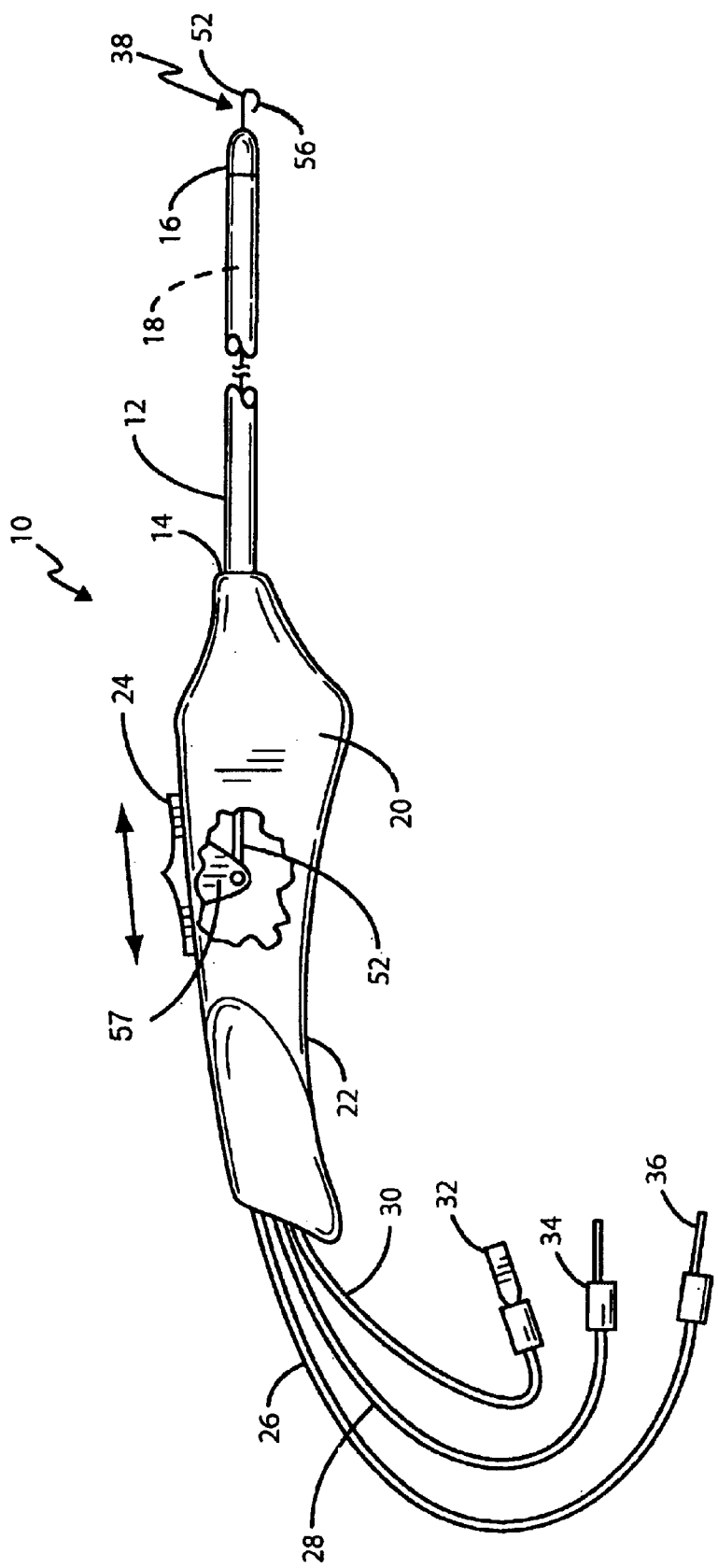
FIG. 1 is a partial side elevation view of the bipolar electrosurgical hook probe comprising a preferred embodiment of the invention.

Referring first to FIG. 1, there is indicated generally by numeral 10 a bipolar electrosurgical hook probe instrument embodying the present invention. It is seen to comprise an elongated tubular barrel 12 whose outside diameter is dimensioned so as to pass through a viewing endoscope or a trocar when used in a minimally invasive surgical procedure. The barrel 12 has a proximal end 14 and a distal end 16 along with a lumen 18 extending therebetween. The tubular barrel 12 may comprise an extruded metal tube of a predetermined length having an electrically insulating coating on its exterior surface. Alternatively, the tubular barrel 12 may be formed from a suitable plastic in an extrusion operation.

Affixed to the proximal end 14 of the tubular barrel 12 is a handle member 20 that is generally longitudinally aligned with the barrel. The handle 20 is ergonomically designed to be grasped with the curved bottom surface 22 lying generally across the joints between the metacarpals and proximal phalanges of a surgeon's hand and with the surgeon's thumb resting on a slide mechanism 24. The handle 20 is preferably molded from a suitable medical-grade plastic and formed interiorly therein is a channel through which electrical conductors 26, 28 and 30 may pass. Affixed to the proximal end of the conductors 26, 28 and 30 are plugs 32, 34 and 36, which are adapted to mate with jacks (not shown) on a standard electrosurgical generator or mode control switch (also not shown).

Figure 2A:
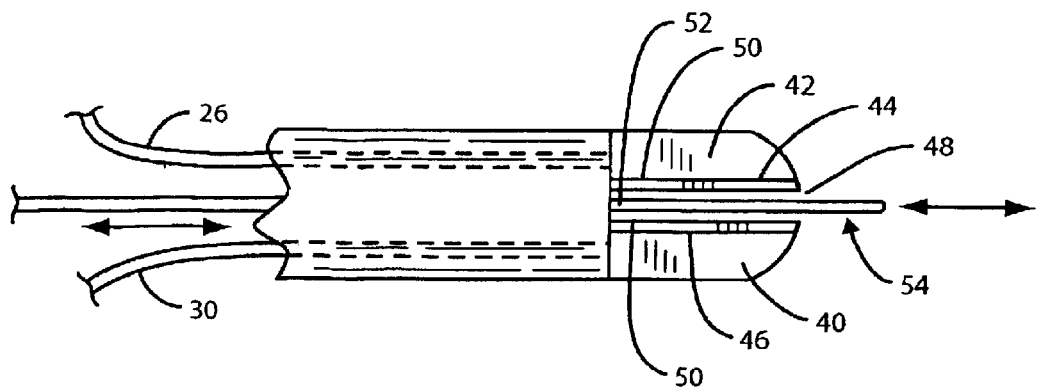
FIG. 2A is a partial view of the distal end portion of the instrument of FIG. 1 with the hook member extended.
Figure 2B:
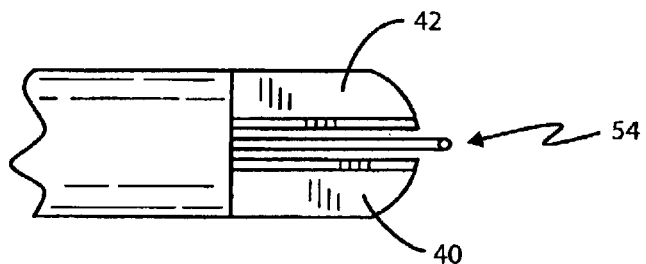
FIG. 2B is a partial view of the distal end portion of the instrument.

Affixed to the distal end 16 of the tubular barrel 12 is an end effector assembly indicated generally by numeral 38. As can be seen from FIG. 1 and from the enlarged view of the distal end portion of the instrument illustrated in FIGS. 2A and 2B, the end effector comprises first and second hemispherical shaped electrodes 40 and 42 which are disposed in parallel, closely spaced but non-contacting relationship to one another and which are fixedly secured to the distal end 16 of the barrel 12. The exterior surface of the electrodes comprises conductive metal. The electrodes may be solid metal or may comprise a ceramic substrate on which a conductive metal layer has been deposited. The walls 44 and 46 that define a slot 48 have an insulating layer 50 thereon. Without limitation, the insulating layers 50 may be a ceramic.

The conductor 26 extends through the handle 20 and through the lumen 18 of the barrel to electrically connect to the electrode 42. Likewise, the conductor 30 also extends through the handle 20 and through the lumen 18 and connects to the electrode 40. It should be recognized that the barrel itself can be metal and can serve as a medium for coupling a voltage to one or the other of electrodes 40 and 42.

Disposed in the slot 48 is the shank portion 52 of a conductive hook-shaped member electrode 54. The distal end portion of the shank 52 is bent to form a hook portion 56 as can best be seen in the view of FIG. 1. The conductor forming the hook electrode 54 extends through the lumen of the tubular barrel 12 and partway through the handle 20 where it is coupled to an ear 56 affixed to the thumb slide 24. Thus, by shifting the thumb slide 24 forward and rearward, the hook portion 57 of the electrode 54 can be made to project from or withdraw into the slot 48. The insulating layers 50 prevent electrical shorting between the hook electrode 54 and the return electrodes 40 and 42. The conductor 28 electrically connects to the shank 52 of the hook.

Figure 3:
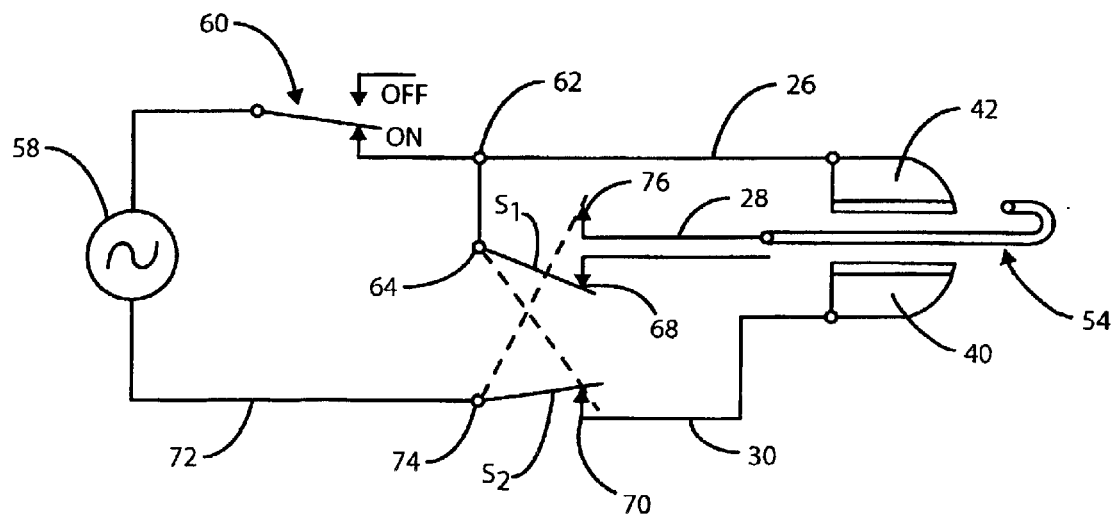
FIG. 3 illustrates a switching circuit for selecting either the cut mode or the coagulation mode of operation.

FIG. 3 illustrates a switching circuit for controlling the mode of operation of the bipolar electrosurgical hook probe comprising a preferred embodiment of the present invention. The switching circuit of FIG. 3 may be resident in the electrosurgical generator used with the instrument or it may be located within the handle 20 of the instrument. Alternatively, the switching arrangement may be physically located in an adapter box disposed between the instrument leads 26, 28 and 30 and a conventional electrosurgical generator.

In the view of FIG. 3, the electrosurgical generator is identified by numeral 58 and it is connected through an on/off switch 60 to a junction point 62 to which the conductor 26 joined to electrode 42 connects. The junction 62 is connected to the pole 64 of a single-pole, double-throw switch having associated with it contacts 68 and 70. Contact 70 is connected to conductor 30 which leads to the electrode 40. The RF generator 58 is also connected by a conductor 72 to a pole 74 of a single-pole, single-throw switch having a contact 76 that is coupled by the conductor 28 to the conductive hook 54.

The switch 60 may be physically located so as to be operable by the surgeon's foot and, when the mode switches are in the coagulation mode, the RF voltage from the generator 58 is applied between the first and second electrodes 40 and 42, with the hook electrode 54 being open circuited. When the mode switches are placed in the cut mode, the voltage from the generator 58 will be applied between the electrodes 40 and 42 together and the hook electrode 54.

When it is desired to use the hook probe 10 to cut through tissue such as a tubular blood vessel or the like, the surgeon loops the hook 56 about the tubular vessel and, by using the thumb slide, draws it against electrodes 40 and 42. The surgeon then applies a first voltage, via switch 60 and the mode selection switches $S_1$ and $S_2$ between the hook electrode 54 and the return electrode, which, as explained above, during cutting, comprise both the first electrode 40 and the second electrode 42 which are maintained at the same potential. Because of the small surface area of the hook electrode compared to the combined surface area of electrodes 40 and 42, a high current density is developed proximate the hook to effect cutting through tissue.

Where it is desired to cut through connective tissue, the hook can be retracted to a point where only the bottom of the hook protrudes out from the slot 48. By applying a cut voltage to the hook electrode and using the coagulation electrodes as a return, the instrument's end can be swept over the tissue causing it to be transected.

To effect coagulation, the hook electrode may be retracted fully within the slot 48 and a potential applied by the generator 58 through switch 60 and switches $S_1$ and $S_2$ between the first electrode 40 and the second electrode 42. As the two electrodes are brought into engagement with the bleeding tissue, the RF current produces sufficient heating over the areas defined by the electrodes 40 and 42 to produce coagulation. In that the electrodes 40 and 42 are of generally equal surface area, either one can function as the active electrode while the other serves as the return electrode. The hook can also be used to catch and draw target tissue into contact with the electrodes 40 and 42 to effect coagulation where the hook remains electrically passive. To cut through the coagulated tissue, then, a cut voltage is applied to the hook electrode while the electrodes 40–42 act as a common return.

The coagulation performed by the instrument of the present invention is significantly more satisfactory than what can be achieved when a hook electrode is used as the active electrode and the return electrode comprises a single slotted hemispherical member as in the Fleenor et al. '435 patent.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A bipolar electrosurgical cutting and coagulating probe, comprising:

(a) an elongated, tubular barrel having a proximal end, a distal end and a lumen extending therebetween;

(b) a handle member affixed to the proximal end of said barrel and including a manually operable actuator member mounted on a surface of the handle member;

(c) an end effector affixed to the distal end of said barrel, said end effector comprising:

(i) first and second electrodes placed in parallel, closely-spaced relationship, each of a relatively large surface area;

(ii) a conductive, reciprocally, longitudinally movable hook member operatively coupled to the actuator member and said hook member having a relatively small surface area compared to the surface areas of the first and second electrodes, the hook member being movable longitudinally in and out of a space between the first and second electrodes upon manipulation of the actuator member; and (d) a plurality of elongated conductors extending through the handle member and into the lumen, one of the conductors connected electrically to the first electrode, another of the conductors connected electrically to the second electrode and still another of the conductors connected electrically to the hook member.

2. The bipolar electrosurgical cutting and coagulating probe as in claim 1 wherein the tubular barrel is a metal having an insulating covering on an exterior surface thereof and an outer diameter sized to fit through a viewing endoscope when said probe is used in a laparoscopic procedure.

3. The bipolar electrosurgical cutting and coagulating probe as in claim 1 wherein the first and second electrodes are hemispherical in shape and of substantially equal surface area.

4. The bipolar electrosurgical cutting and coagulating probe as in claim 3 wherein the first and second electrodes have a rounded distal end.

5. The bipolar electrosurgical cutting and coagulating probe as in claim 1 wherein a voltage is applied between said one conductor and said another conductor to coagulate tissue being contacted by the first and second electrodes and a voltage is applied between said another of the conductors and both said one conductor and said another conductor to cut through tissue being contacted by the hook member.

6. The bipolar electrosurgical cutting and coagulating probe as in claim 5 and further including:

(a) switching means for selectively applying the voltage between either the said one and the said another of the conductors or between said still another and both said one and said another of the conductors.

7. The bipolar electrosurgical cutting and coagulating probe as in claim 6 wherein the switching means is located on the handle member.

8. The bipolar electrosurgical cutting and coagulating probe as in claim 6 wherein the switching means is a foot-actuated switch.

9. The bipolar electrosurgical cutting and coagulating probe as in claim 6 wherein the voltage is produced by an electrosurgical generator and the switching means is located on the electrosurgical generator.

10. The bipolar electrosurgical cutting and coagulating probe as in any one of claims 1–9 and further including means for electrically isolating the conductive hook member from the first and second electrodes to prevent an electrical short therebetween.

11. The bipolar electrosurgical cutting and coagulating probe as in claim 10 wherein opposed wall surfaces on the first and second electrodes define said space and the means for electrically isolating the conductive hook member from the first and second electrodes comprises an electrically insulating layer on said opposed wall surfaces.

12. The bipolar electrosurgical cutting and coagulating probe as in claim 11 wherein the electrically insulating layer is a ceramic material.

13. The bipolar electrosurgical cutting and coagulating probe as in claim 1 wherein the actuator member is slidable relative to the handle member.

* * * * *